United States Patent [19]

McAlpine

[11] 4,214,076
[45] Jul. 22, 1980

[54] 2'-N-SUBSTITUTED FORTIMICIN B AND DERIVATIVES

[75] Inventor: James B. McAlpine, Libertyville, Ill.

[73] Assignee: Abbott Laboratories, North Chicago, Ill.

[21] Appl. No.: 863,013

[22] Filed: Dec. 21, 1977

[51] Int. Cl.² ............... A61K 31/71; C07H 15/22
[52] U.S. Cl. ..................... 536/17 R; 424/180; 536/4
[58] Field of Search ..................... 536/17, 13, 4

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 3,985,727 | 10/1976 | Daniels | 536/17 |

Primary Examiner—Johnnie R. Brown
Attorney, Agent, or Firm—Robert L. Niblack; Gildo E. Fato; Joyce R. Niblack

[57] ABSTRACT

2'-N-substituted fortimicin B and fortimicin B derivatives represented by the formula

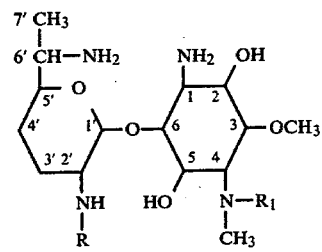

wherein: R is selected from the group consisting of β-naphthoyl, γ-naphthoyl, γ-naphthyl, (γ-amino-γ-hydroxybutyryl) or 1-(2-amino-4-hydroxybutyl) and $R_1$ is N-monoloweralkylaminoacyl, N,N-diloweralkylaminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl or hydrogen and the pharmaceutically acceptable salts thereof; pharmaceutical compositions containing the compounds; and methods of making and using the compounds. The compounds are useful as antibiotics.

1 Claim, No Drawings

2'-N-SUBSTITUTED FORTIMICIN B AND DERIVATIVES

BACKGROUND OF THE INVENTION

It is known that the antibacterial and pharmacological properties of many naturally produced aminoglycoside antibiotics can be altered by structural modifications. For example, certain chemical modifications in the gentamicin and kanamycin family of aminoglycoside antibiotics provide compounds which are less toxic than the parent antibiotic. Further, in the same family series mentioned above, certain modifications alter the antibacterial spectrum advantageously either by increasing the intrinsic activity or increasing activity against resistant strains.

Historically, once an aminoglycoside antibiotic has been in clinical use for awhile, resistant microorganisms arise. In many cases, the resistance is R-factor mediated and is attributed to the ability of the bacteria to enzymatically modify the amino or hydroxyl groups of the aminoglycoside antibiotic. Thus there is a continuing need for new fortimicin antibiotic entities.

The present invention provides new and useful fortimicin derivatives.

SUMMARY OF THE DISCLOSURE

Novel 2'-N-substituted fortimicin B derivatives are provided by this invention as well as their salts, intermediates, processes for making the compounds, and compositions and methods employing the compounds.

The fortimicin derivatives of this invention are antibiotics which are effective against various Gram-negative and Gram-positive bacteria and can be administered orally or parenterally in daily dosages of from about 10 to about 200 mg/kg of body weight daily to mammalian patients showing symptoms of infection caused by one of the susceptible bacteria.

The compounds can also be used as preservatives for various industrial solutions, in antibacterial scrub solutions for cleaning laboratory bench tops and the like. They are also useful as intermediates in preparing other fortimicin B derivatives which have anti-bacterial activity.

The base fortimicin derivatives of this invention are amines and form salts with fluosilicic acid which are useful as mothproofing agents according to the teachings of U.S. Pat. Nos. 1,915,334 and 2,075,359. They also form salts with thiocyanic acid which condense with formaldehyde to form resinous materials useful as pickling inhibitors as taught in U.S. Pat. Nos. 2,425,320 and 2,606,155.

Derivatives useful in the preparation of the compounds of this invention are provided as well as method of making and using the compounds and compositions employing the compounds.

DETAILED DESCRIPTION OF PREFERRED EMBODIMENTS

The present invention provides 2'-N-substituted fortimicin B and derivatives represented by the formula:

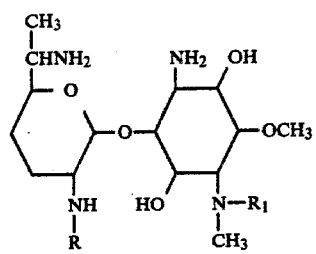

wherein R is β-naphthoyl, γ-naphthoyl, γ-naphthyl, α-amino-γ-hydroxybutyryl or 1-(2-amino-4-hydroxybutyl); and $R_1$ is acyl, aminoacyl, N-monoloweralkylaminoacyl, N,N-diloweralkyl-aminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, and the pharmaceutically acceptable salts thereof.

The term "pharmaceutically acceptable salts" refers to non-toxic acid addition salts of the compounds of this invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

The term "acyl" refers to groups represented by the formula

wherein $R_1$ is loweralkyl, i.e., acetyl, propionyl, butyryl, etc.

"Lower alkyl" refers to straight or branched chain alkyl radicals having from 1 to 6 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl and the like.

The term "amino acid residue" refers to D, L or DL amino acid residues and includes but is not limited to glycyl, alanyl, sarcosyl, tyrosyl, phenylalanyl, methionyl, seryl, lysyl, asparaginyl, isoleucyl, leucyl, histidyl, threonyl, aspartyl, asparaginyl, valyl, prolyl, glutaminyl, tryptophanyl, glutamyl and the like.

The 2'-N-derivatives of this invention can be prepared by reacting fortimicin B with tert-butyl-S-(4,6-dimethyl-pyrimidin-2-yl) thiolcarbonate to obtain the 2'-tert-butyloxycarbonyl (Boc) fortimicin B intermediate.

The 2'-Boc-intermediate is then reacted with a suitable acylating agent, i.e., N-(benzyloxycarbonyloxy)-succinimide which results in the 1,6'-di-N-benzyloxy-2'-Boc-fortimicin B intermediate.

Treatment of this intermediate with an active ester of an N-protected desired 4-N-substituent, e.g., the N-hydroxysuccinimide ester of N-benzyloxycarbonyl glycine gives the 2'-N-Boc-per-N-protected 4-N-substituted fortimicin B, i.e. when the 4-N-substituent is N-protected glycine this is a fortimicin A derivative. The 2'-N-Box group is then conveniently removed from either the 1,6'-di-N-benzyloxycarbonyl-2'-N-Boc fortimicin B or from the 2′-N-Boc-per-N-protected-4-N-substituted fortimicin B by treatment with trifluoroacetic acid.

2′-N-Akylation or acylation is then conveniently accomplished by reacting the 2′-deprotected intermediate with a suitable aldehyde (R,CHO) in the presence of sodium borohydride or by treatment with a carboxylic acid ester as described above. Deprotection is then completed by hydrogenolysis in the presence of 5% palladium on carbon catalyst which results in the desired 2′-alkyl or 2′-acyl derivatives. Representative compounds include:

2′-N-β-naphthoylfortimicin B;
2′-N-β-naphthoylfortimicin A;
2′-N-γ-naphthoylfortimicin B;
2′-N-γ-naphthoylfortimicin A;
2′-N-β-naphthylfortimicin B;
2′-N-β-naphthylfortimicin A;
2′-N-γ-naphthylfortimicin B;
2′-N-γ-naphthylfortimicin A;
2′-N-(γ-amino-γ-hydroxybutyryl)fortimicin B;
2-N-(γ-amino-γ-hydroxybutyryl)fortimicin A;
2-N-1-(2-amino-4-hydroxybutyl)fortimicin B;
2-N-1-(2-amino-4-hydroxybutyl)fortimicin A;
and the like compounds and their pharmaceutically acceptable salts.

The compounds of this invention are active as systemic antibiotics when injected by parenteral routes of administration, i.e., by the intramuscular, intravenous, intraparitoneal or subcutaneous routes of administration. The compounds can also be administered orally in those instances where it is desirable to sterilize the intestional tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 10 to 200 mg/kg of body weight daily are administered to a mammalian patient suffering from an infection caused by susceptable organism.

The antibacterial activity of the compounds of this invention is initially determined by a two-fold dilution test using Meuller-Hinton agar, 10 ml per Petri plate. The inoculum of approximately $1 \times 10^5$ of the indicated test organism is delivered by the Steer's replicator. The test is incubated at 37° C. for 24 hours.

I claim:
1. 2′-N-substituted naphthyl Fortimicins B of the formula

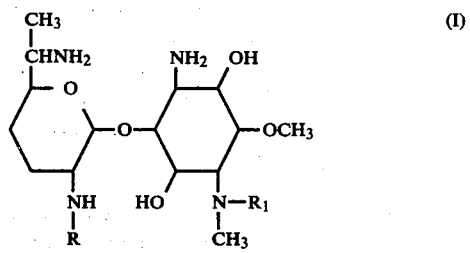

wherein R is β-naphthoyl, γ-naphthoyl, γ-naphthyl; and $R_1$ is acyl, aminoacyl, N-monoloweralkylaminoacyl, N,N-diloweralkyl-aminoacyl, hydroxy-substituted aminoacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, and the pharmaceutically acceptable salts thereof.

* * * * *